United States Patent [19]

Thorogood

[11] 4,431,815

[45] Feb. 14, 1984

[54] 1-[3-(2,4-DICHLOROPHENYL)PROPYL-]IMIDAZOLE AND SALTS THEREOF

[75] Inventor: Peter B. Thorogood, London, England

[73] Assignee: Burroughs Wellcome Co., Research Triangle Park, N.C.

[21] Appl. No.: 462,769

[22] Filed: Feb. 1, 1983

Related U.S. Application Data

[63] Continuation of Ser. No. 67,406, Aug. 17, 1979, abandoned, which is a continuation-in-part of Ser. No. 008,101, Jan. 31, 1979, abandoned, which is a continuation-in-part of Ser. No. 952,774, Nov. 19, 1978, abandoned, which is a continuation-in-part of Ser. No. 936,406, Aug. 24, 1978, Pat. No. 4,284,641.

[51] Int. Cl.$^3$ .......................................... C07D 233/56
[52] U.S. Cl. ................................ 548/335; 424/273 R; 542/458; 542/468; 548/346
[58] Field of Search ........................................ 548/335

[56] References Cited

U.S. PATENT DOCUMENTS

| | | | |
|---|---|---|---|
| 3,769,422 | 10/1973 | Timmler et al. | 548/335 X |
| 3,927,017 | 12/1975 | Heeres et al. | 548/335 |
| 4,006,243 | 2/1977 | Strehlke et al. | 424/273 R X |
| 4,085,209 | 4/1978 | Miller et al. | 424/273 R X |
| 4,105,762 | 8/1978 | Miller et al. | 548/335 X |

OTHER PUBLICATIONS

Baggaley, K., et al., *J. Med. Chem.*, 18(8), 833–836 (1975).

*Primary Examiner*—Richard A. Schwartz
*Attorney, Agent, or Firm*—Donald Brown

[57] ABSTRACT

A method for (i) the treatment or prophylaxis of a thrombo-embolic disorder of a mammal or a mammalian tissue (ii) the prevention, treatment or prophylaxis of angina pectoris, or (iii) the prevention or delay of the onset of shock, which comprises the administration to the mammal or mammalian tissue of a non-toxic, effective amount of an imidazole of the formula:

$$\text{imidazole}-N-(A)_n-R \quad (I)$$

in which A is a straight or branched, saturated or unsaturated acyclic hydrocarbon radical of from 1 to 3 carbon atoms, n is 0 or 1, and R is $$\text{phenyl}-(Q)_m$$

wherein m is 0 or an integer which is at least 1 and the or each Q substituent, which, when m is greater than 1 may be the same or different is selected from a saturated or unsaturated hydrocarbon group of from 1 to 4 carbon atoms; alkoxy of from 1 to 4 carbon atoms; nitro; phenyl; acyloxy; halo; trihalomethyl; hydroxy; carboxyl; a salt of such a carboxyl group; carboalkyloxy; carboaryloxy; carboarylalkyloxy; $-NR^6R^7$ and $-CONR^6R^7$, in which $R^6$ and $R^7$ may be the same or different and are each hydrogen or alkyl of from 1 to 4 carbon atoms; the imidazole being the free base or a pharmaceutically acceptable salt thereof.

Pharmaceutical formulations of some inidazoles within the class suitable for use in the method of treatment are also novel. Methods of preparing the imidazoles are provided.

2 Claims, No Drawings

1-[3-(2,4-DICHLOROPHENYL)PROPYL-]IMIDAZOLE AND SALTS THEREOF

CROSS-REFERENCE TO EARLIER APPLICATIONS

This is a continuation of application Ser. No. 067,406 filed Aug. 17, 1979, now abandoned, which is a continuation-in-part of (i) application Ser. No. 8,101 filed Jan. 31, 1979, now abandoned, and (ii) application Ser. No. 952,774, filed Oct. 19, 1978, now abandoned, which is in turn a continuation-in-part of application Ser. No. 936,406 filed Aug. 24, 1978, now U.S. Pat. No. 4,284,641.

The present invention relates to imidazole derivatives and salts thereof, to their synthesis and intermediates therefor, to pharmaceutical formulations containing such compounds and to the use of these compounds in medicine.

Thromboxane $A_2$ (TXA$_2$), a potent stimulator of blood platelet aggregation, is produced in platelets, from the prostaglandin endoperoxides PGG$_2$ and PGH$_2$. Prostacyclin (PGI$_2$), which has potent anti-aggregatory activity, is also produced (in blood vessel walls) from PGG$_2$ and PGH$_2$, and it has been suggested that a balance between the production of TXA$_2$ and PGI$_2$ is the controlling factor in thrombus formation. It would, in consequence, be desirable in the treatment and prophylaxis of thrombo-embolic disorders to be able to selectively inhibit TXA$_2$ synthetase, and thereby favour the production of the anti-aggregatory agent PGI$_2$.

Imidazole and 1-methylimidazole are known to provide some degree of inhibition of the enzymic conversion of the endoperoxides (PGG$_2$ and PGH$_2$) to thromboxane $A_2$ by platelet microsomes (Moncada et al., Prostaglandins, 13/4, 611–618, 1977). Certain 1-n-alkylimidazoles, especially 1-n-dodecylimidazole and its higher homologues have been described as being capable of lowering serum cholesterol levels (U.K. Pat. No. 1,364,312; Biochem. Pharmacol. 24, 1902–1903, 1975).

We have now discovered that TXA$_2$ synthetase may be inhibited by 1-substituted imidazoles of formula (I), e.g. 1-arylalkylimidazoles, and acid addition salts thereof. The compounds of formula (I) and their salts are hereinafter referred to as the "active compounds".

The compounds of formula (I) are:

(I)

in which
A is a straight or branched, saturated acyclic hydrocarbon radical of 1, 2 or 3 carbon atoms, or a straight or branched, unsaturated acyclic hydrocarbon radical of 2 or 3 carbon atoms;
n is 0 or 1, and
R is

wherein m is 0 or an integer which is at least 1 and the or each Q substituent, which, when m is greater than 1, may be the same or different is selected from a saturated hydrocarbon group of from 1 to 4 carbon atoms; an unsaturated hydrocarbon group of from 2 to 4 carbon atoms; alkoxy of from 1 to 4 carbon atoms; nitro; phenyl; acyloxy; halo; trihalomethyl; hydroxy; carboxyl; a salt of such a carboxyl group; carboalkyloxy; carboaryloxy; carboarylalkyloxy; —NR$^6$R$^7$ and CONR$^6$R$^7$, in which R$^6$ and R$^7$ may be the same or different and are each hydrogen or alkyl of from 1 to 4 carbon atoms; or, optionally, cyano (with the proviso that, when n is 0, m is at least 1).

A class of novel compounds within the scope of formula (I) is of the formula:

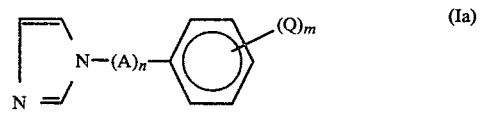
(Ia)

in which A is a straight or branched, saturated acyclic hydrocarbon radical of 1, 2 or 3 carbon atoms or a straight or branched unsaturated acyclic hydrocarbon radical of 2 or 3 carbon atoms, n is 1 and m is an integer which is at least 1, and the or each Q substituent, which when m is greater than 1 may be the same or different, is selected from a saturated hydrocarbon group of from 1 to 4 carbon atoms or an unsaturated hydrocarbon group of from 2 to 4 carbon atoms with the proviso that, (a) when A is a methylene or ethylidene group, m is at least 2 when each Q is a saturated hydrocarbon group
(b) when A is a branched propylene or straight propylidene group, m is at least 3 when each Q is saturated hydrocarbon group,
(c) when the group A is unsaturated, Q may also be selected from alkoxy of from 1 to 4 carbon atoms; halo; trihalomethyl; hydroxy; carboxyl; a salt of such a carboxyl group; carboalkyloxy; carboaryloxy, carboarylalkyloxy; —NR$^6$R$^7$ or —CONR$^6$R$^7$, in which R$^6$ and R$^7$ may be the same or different and are hydrogen or alkyl of from 1 to 4 carbon atoms; with the further proviso that when m is 1, Q is not a saturated hydrocarbon group;

the imidazole being the free base or an acid addition salt thereof, preferably a pharmaceutically acceptable salt.

In formula (Ia) examples of the group A are methylene, ethylene, propylene and in the orientation of formula (Ia), —CH$_2$—CH=CH— (cis or trans or a cis/trans isomeric mixture).

A valuable class of compounds of formula (Ia) are those in which the aromatic ring is substituted by at least two groups Q, preferably saturated or unsaturated hydrocarbon groups, e.g. alkyl or alkenyl groups, especially if one substituent is in the 4-position in the benzene ring, and A is either methylene (—CH$_2$—) or in the orientation of formula (I), —CH$_2$—CH=CH— (cis or trans or cis/trans isomeric mixture-cinnamyl compounds.) A particularly preferred class of novel imidazoles is those of formula (Ic):

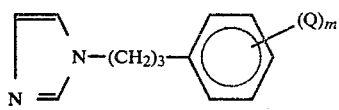 (Ic)

wherein Q is halo, preferably chloro, and m is at least 2, and is preferably 2; the imidazole being the free base or an acid addition salt, which is preferably pharmaceutically acceptable. The compound 1-(3-(2,4-dichlorophenyl)propyl)-imidazole is particularly preferred.

Another particularly preferred class of novel imidazoles is those of formula (Id):

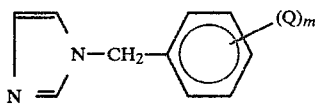 (Id)

wherein Q is halo, preferably chloro and especially bromo, and m is at least 1; the imidazole being the free base or an acid addition salt thereof. Preferably there is at least one group Q in a position ortho or meta to the —CH₂— group; especially preferred are compounds wherein m is 1 and the group Q is ortho or meta to the —CH₂— group. The compound 1-(2-bromobenzyl)imidazole is particularly preferred.

When A is unsaturated, preferred compounds of formula (Ia) are those in which the aromatic ring contains alkyl, chloro or methoxy substituents.

Compounds of formula (Ia) may also be used a acid addition salt thereof, especially as pharmaceutically acceptable ones.

Especially preferred compounds include:

1-(3,4-dimethylbenzyl)imidazole,
1-(2,4,6-trimethylbenzyl)imidazole,
1-(3-(2,4-dichlorophenyl)propyl)imidazole,
1-(2,4-dichlorocinnamyl)imidazole,
i.e. 1[3-(2,4-dichlorophenyl)prop-2-enyl]imidazole
1-[3-(2,6-dichlorophenyl)prop-2-enyl]imidazole and acid addition salts thereof.

Other preferred compounds include:

1-[3-(3,4,5-trimethoxyphenyl)prop-2-enyl]imidazole
1-[3-(3,4-dimethoxyphenyl)prop-2-enyl]imidazole,
1-[3-(2-hydroxyphenyl)prop-2-enyl]imidazole,
1-[3-(3-bromophenyl)prop-2-enyl]imidazole,
1-[3-(4-chlorophenyl)prop-2-enyl]imidazole,
1-[3-(3,4-dimethylphenyl)prop-2-enyl]imidazole,
1-[3-(2-methoxyphenyl)prop-2-enyl]imidazole,
and acid addition salts thereof.

The present invention also provides a method for (i) the treatment or prophylaxis of a thrombo-embolic disorder of a mammal or a mammalian tissue, (ii) the prevention, treatment or prophylaxis of angina pectoris, or (iii) the invention or delaying of the onset of shock, comprising the administration to the mammal or mammalian tissue of a non-toxic, effective amount of an imidazole of the formula

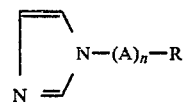 (Ib)

in which
A is a straight or branched, saturated acyclic hydrocarbon radical of 1, 2 or 3 carbon atoms, or a straight or branched unsaturated acyclic hydrocarbon radical of 2 or 3 carbon atoms;
n is 0 or 1; and
R is

wherein m is 0 or an integer which is at least 1 and the or each Q substituent, which, when n is greater than 1, may be the same or different, is selected from a saturated hydrocarbon group of from 1 to 4 carbon atoms; an unsaturated hydrocarbon group of from 2 to 4 carbon atoms; alkoxy of from 1 to 4 carbon atoms; nitro; phenyl; acyloxy; halo; trihalomethyl; hydroxy; carboxyl; a salt of such a carboxyl group; carboalkyloxy; carboaryloxy; carboarylalkyloxy; —NR⁶R⁷ and —CONR⁶R⁷, in which R⁶ and R⁷ may be the same or different and are each hydrogen or alkyl of from 1 to 4 carbon atoms (with the proviso that, when n is 0, m is at least 1); the imidazole being the free base or a pharmaceutically acceptable acid addition salt thereof.

The compounds, i.e. the classes of compounds and the specifically identified compounds within the scopes of formulae (I), and (Ia) referred to hereinbefore may be used in this method of treatment. The following specifically named compounds within the scope of formula (Ib) may also be used.

Especially preferred compounds are:

1-(2-bromobenzyl)imidazole
1-benzylimidazole and
1-(2,4-dichlorobenzyl)imidazole, as well as
1-[3-(2,4-dichlorophenyl)propyl]imidazole,
1-(2,4,6-trimethylbenzyl)imidazole, as well as
1-(3,4-dimethylbenzyl)imidazole already mentioned.

Other preferred compounds include:

1-(2-phenylethyl)imidazole,
1-(3-phenylpropyl)imidazole,
1-(3-phenylprop-2-enyl)imidazole,
1-(2-phenylpropyl)imidazole,
1-(3-nitrobenzyl)imidazole,
1-(3-aminobenzyl)imidazole,
1-(4-fluorobenzyl)imidazole,
1-(4-methylbenzyl)imidazole,
1-(2-bromobenzyl)imidazole,
1-(4-bromobenzyl)imidazole,
1-(3-bromobenzyl)imidazole,
1-(4-i-propylbenzyl)imidazole,
and pharmaceutically acceptable acid addition salts thereof.

In general the compounds containing the substituent Q as hereinbefore defined are preferred when the substituent Q is, where possible, selected from the group consisting of methyl, chloro, fluoro, methoxy, ethoxy, benzoyloxy, carboethoxy and trifluoromethyl. Similarly, where possible, m may be 1, 2 or 3, and is preferably at least 2, especially when there is a substituent in the 4-position in the benzene nucleus.

In contrast to imidazole and 1-methyl-imidazole the compounds of formula (I) are more potent inhibitors of TXA$_2$ synthetase. Many of the compounds (for example in (I), when A is —CH$_2$—, or, in the orientation of formula (I), —CH$_2$—CH$_2$—CH=CH—) are also more selective in their action in not inhibiting other anti-aggregatory prostaglandin generating enzymes. The compounds of formula (I) also do not produce the side-effects found with imidazole upon in vivo administration. The compounds of formula (I) are further capable of inhibiting platelet aggregation in vivo and also are capable of disaggregating platelet clumps, the compounds 1-(3,4-dimethylbenzyl)imidazole, 1-(2,4,6-trimethylbenzyl)imidazole, 1-benzylimidazole and 1-(2,4-dichlorobenzyl)imidazole, 1-(3-(2,4-dichlorophenyl)propyl)imidazole, and their salts especially displaying these properties.

The compounds of formula (I) are suitable for use in the treatment or prophylaxis of angina pectoris. In some cases it is possible to prevent the onset of angina pectoris, for example when a patient with coronary artery disease is given cardiac pacing, which leads generally to an increase of TXA$_2$ in the blood, and which is associated with the onset of angina pectoris. Also, inhibition of TXA$_2$ formation prevents or delays the onset of shock, e.g. experimentally induced shock in laboratory animals.

Known compounds of formula (I) that may be used in the methods of treatment of this invention include:

1-(3-nitrophenyl)imidazole,
1-(3-fluorophenyl)imidazole,
1-(4-methylphenyl)imidazole,
1-(2-methylphenyl)imidazole,
1-(4-bromophenyl)imidazole,
1-(4-methoxyphenyl)imidazole,
1-(2-trifluoromethylphenyl)imidazole,
1-(3-trifluoromethylphenyl)imidazole,
1-(4-trifluoromethylphenyl)imidazole,
1-(2,3-dimethylphenyl)imidazole,
1-(3-bromophenyl)imidazole,
1-(4-cyanophenyl)imidazole,
1-(2-fluorophenyl)imidazole,
1-(4-fluorophenyl)imidazole, 1-(2-nitrophenyl)imidazole,
1-(2-nitro-4-methylphenyl)imidazole,
1-(2-nitro-4-chlorophenyl)imidazole,
1-(2-nitro-4-methoxyphenyl)imidazole,
1-(2,6-dimethylphenyl)imidazole,
1-(2-isopropylphenyl)imidazole
1-(2-ethylphenyl)imidazole,
1-(2,6-diethylphenyl)imidazole,
1-(3-methylphenyl)imidazole,
1-(2,4,6-trimethylphenyl)imidazole,
1-(2,6-di-isopropylphenyl)imidazole,
1-(2,4-diethylphenyl)imidazole,
1-(2,4-dimethylphenyl)imidazole,
and their pharmaceutically acceptable acid addition salts.

These 1-(substituted-phenyl)imidazoles may be prepared by the method described by A. L. Johnson et al., J. Med. Chem. 12(6) 1024–8 (1969).

Imidazoles of formula (I) and acid addition salts thereof may be made by any method known in the art for the synthesis of compounds of analogous structure. In general these methods comprise linking the imidazole ring to the remainder of the molecule; converting a precursor molecule by elimination of a functional group from the imidazole ring; and formation of the desired compound from a corresponding pyrazole, imidazoline, or other unsaturated analogue.

A most convenient method of synthesis involves the reaction of imidazole (formula II) or a salt thereof with an alkylating, alkenylating or arylating agent of formula (III):

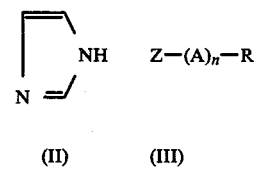

(II)        (III)

wherein R, n and A are as defined in formula (I) and Z is a leaving group. This reaction is well established in the literature, and the leaving group may be chosen from a variety of substituents but especially halo, preferably chloro or bromo, or from p-toluenesulphonyloxy but other arylsulphonyloxy, alkanesulphonyloxy or aralkylsulphonyloxy radicals may be used. The reaction is preferably performed in the presence of an acid acceptor, for example an alkali metal alkoxide, such as sodium methoxide or potassium tertiary butoxide in the presence of an alkanol. The leaving group Z may itself be formed in situ from the corresponding alkanol (Z=OH) by reaction with a hydrohalogenic acid (e.g. hydrochloric acid or a Lewis acid, such as aluminium chloride: see Japanese Patent No. 131577/77) and the resulting agent of formula (III) reacted directly with imidazole without prior isolation. When Z is halo, the reaction may be carried out in the presence of a copy catalyst, e.g. as in Ullmann reaction, especially when n is 0. Alternatively an alkanol (Z=OH) or a derivative thereof (e.g. Z=R—A—O) may be reacted directly with imidazole (II) by heating in the presence of a dehydrating agent such as phosphoric acid, or a phosphate (see Japanese Patent Publication No. 51 105 060), sulphuric acid or sulphates (see Japanese Patent Publication No. 51 105 061).

Among precursor molecules which may be converted to a compound of formula (I) or an acid addition salt thereof, are substituted imidazole derivatives of formula (IV), or addition salts thereof;

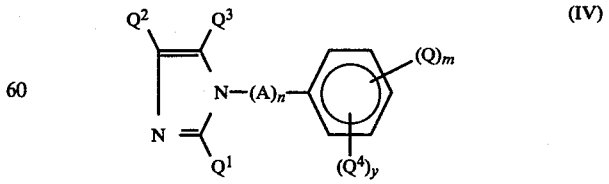

wherein A, m, n and Q are as defined in formula (I) and $Q^1$, $Q^2$, $Q^3$ and $Q^4$ are the same or different, at least one being a radical capable of removal by, for example, reduction or oxidation, the remaining radical or radicals being selected from hydrogen or a radical capable of removal in the same or another manner as the removable radical (e.g. a carboxyl group—see formula (VI)—removed by decarboxylation) y is 0 or an integer, with the proviso that y and m together do not exceed 5. $Q^1$, $Q^2$, $Q^3$ and $Q^4$ may be selected for example from thio (—SH), alkylthio (S-alkyl, wherein alkyl has from 1 to 4 carbon atoms) or halo, preferably chloro or bromo. The reaction conditions are chosen according to the nature of the radicals $Q^1$, $Q^2$, $Q^3$ and $Q^4$. Desulphurisation may be performed by oxidative or reductive procedures using for example nitric acid or Raney nickel; and reductive dehalogenation by the use of zinc and acetic acid or Raney nickel or other reagents known in the art or described in the literature.

Another class of examples include carboxyimidazoles or derivatives thereof of formula (VI):

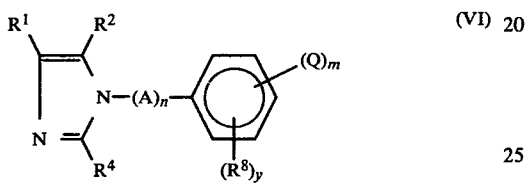
(VI)

wherein A, m, n, Q and y are as defined in formula (IV) at least one of $R^1$, $R^2$, $R^4$ and $R^8$ is carboxyl or a derivative thereof (for example an ester such as an alkyl ester, an acid halide such as the chloride, or the nitrile) and the other is, or the others are independently, hydrogen or carboxyl or a derivative as described. The compounds of formula (VI) may be converted into the imidazoles of formula (I) by any suitable decarboxylation conditions which may simply comprise heating the compounds with or without a catalyst such as copper.

The imidazoles of formula (I) may also be made from a compound of formula (VII):

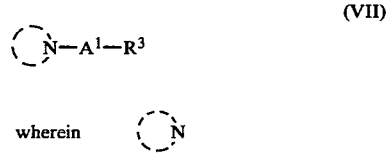
(VII)

wherein 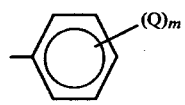

is 1-imidazoline, 1-imidazole or 1-pyrazole, $A^1$ is a bond or straight or branched saturated or unsaturated acyclic hydrocarbon radical which may include a keto group, and $R^3$ is

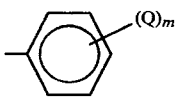

as defined in formula (I), or when A is unsaturated Q may be nitro, provided that at least one of

$A^1$ and $R^3$ is other than 1-imidazole, bond or saturated or unsaturated acyclic hydrocarbon and respectively as defined in formula (I). Thus an imidazoline (VIII)

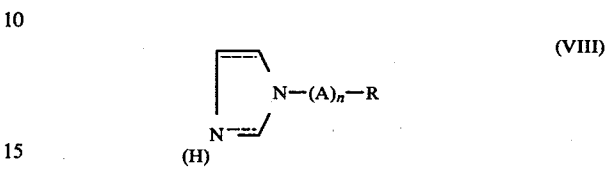
(VIII)

wherein one of - - - represents an extra bond and, A, n and R are as defined in formula (I) may be dehydrogenated to the corresponding imidazole in the presence of a catalyst, for example by heating to 250° C. in the presence of palladium, nickel or platinum under pressure, or by heating with a dehydrogenating agent, such as selenium or copper oxide. 1-Pyrazole compounds (VII) may be treated with ultra-violet radiation, optionally under an inert atmosphere (e.g. argon) in for example 1, 2-dimethoxyethane at room or elevated temperatures (see for example "Ring Transformations of Heterocycles" edited van der Plas, Academic Press, 1973 at page 261). The unsaturated imidazoles of formula (I) (in formula (VII), $A^1$ and/or Q (within $R^3$) are unsaturated) may be reduced to the corresponding less saturated or completely saturated compounds (but not reducing any aromatic nucleus e.g. by hydrogenation with a noble metal catalyst, for example platinum or palladium in an alkanol. If Q is amino in the final product then its precursor may be a nitrogen-containing group reducible to amino, e.g. nitro. A compound of, for example, formula

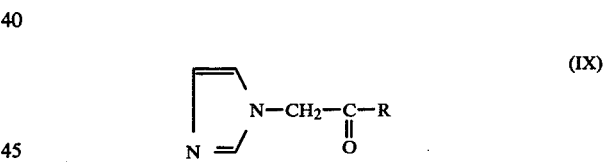
(IX)

where R is as defined in formula (I), may be reduced at the keto group to a —CH$_2$— group for example by a Clemmensen reduction.

When one or more of the Q groups is an alkyl or alkenyl group it may be introduced into the phenyl ring by a Friedel Crafts or similar Lewis-acid catalysed reaction of the type

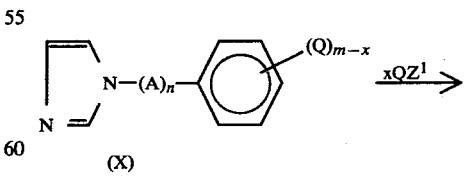
(X)

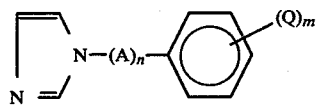
(I)

wherein A, Q, m and n are as defined for formula (I), x is an integer less than or equal to m and $Z^1$ is a leaving group, e.g. halo, suitable for use in this type of reaction.

Compounds of formula (I) may also be prepared by cyclising, preferably in the presence of an acid acceptor, a compound of formula

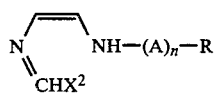
(XI)

wherein A, n and R are as defined for formula (I) and $X^2$ is a leaving group.

Compounds of formula (I) may also be prepared by reacting a compound of formula

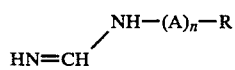
(XII)

wherein A, n and R are as defined for formula (I) with a compound of formula:

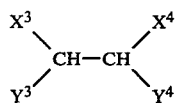
(XIII)

wherein either of $X^3$ and $Y^3$ is a leaving group such as halo or hydroxy and the other is hydrogen or $X^3$ and $Y^3$ are both halo or together with the carbon atom to which they are attached form an aldehyde group or an acetal derivative thereof e.g. both $X^3$ and $Y^3$ are alkoxy, and $X^4$ and $Y^4$ are as defined for $X^3$ and $Y^3$, although they may be the same as or different from $X^3$ and $Y^3$.

An imine salt of for example formula:

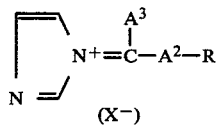
(XIIIa)

(wherein R is as defined for formula (I), $X^-$ is an anion, $A^2$ is a chemical bond or a straight or branching, saturated or unsaturated acyclic hydrocarbon radical, which may include a keto group, $A^3$ is hydrogen or a saturated or unsaturated acyclic hydrocarbon radical, which may include a keto group, with the proviso that $A^2$ and $A^3$ together contain no more than 2 carbon atoms), may be reduced to the corresponding compound of formula (I) by e.g. zinc and a mineral acid, e.g. hydrochloric acid.

The intermediates for use in the above described reactions may also be made by conventional methods known in the art. Thus the 1-pyrazole and 1-imidazoline intermediates (formula (VII)) may be prepared by alkylation of pyrazole and imidazoline in an analogous manner to that described above for preparation of the corresponding imidazoles. The intermediates of formula (III) may be made in known manner preferably by halogenation of the corresponding alcohols (formula (III), Z――OH). When A is unsaturated with three carbon atoms, the alcohol may be prepared from paraformaldehyde and the corresponding unsaturated A compound with two carbon atoms by analogy with the method described in *Bull. Chem. Soc.* Japan 46/48, 2512-5, (1973). The substituted imidazole intermediates of formula (IV) may be made in known manner, for example see "Imidazole and its derivatives" Part 1, Ed. K. Hoffmann, Interscience Publishers Inc. New York, 1973. For example the 2-thioimidazoles of formula (IV) may be made by cyclisation of an acetal of formula (XIV):

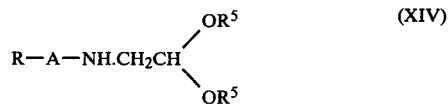
(XIV)

with thiocyanate, wherein $R^5$ is alkyl, aryl or arylalkyl.

The pharmaceutically acceptable addition salts of the compounds of formula (I) may be prepared by any method known in the art. In particular they may be prepared by treating the parent imidazole with the appropriate acid.

Examples of the addition salts of the compounds of formula (I) include those salts derived from the following acids: oxalic, hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic and benzenesulphonic.

The imidazoles of formula (I) may be used in conjunction with a phosphodiesterase inhibitor, which provides a further, synergistic increase in effect, as it acts against platelet aggregation by a different pathway.

Suitable (cyclic AMP) phosphodiesterase inhibitors for use in potentiating the anti-aggregatory effects of the active compounds include as such or as pharmaceutically acceptable salts:

(a) Xanthine derivatives such as:

Theophylline (3,7-dihydro-1,3-dimethyl-1$\underline{H}$-purine-2,6-dione), and salts thereof 3-Isobutyl-1-methyl-xanthine;

Caffeine(3,7-dihydro-1,3,7-trimethyl-1$\underline{H}$-purine-2,6-dione) and salts thereof; and Aminophylline (adduct of Theophylline and 1,2-ethanediamine (2:1)).

(b) Isoquinoline derivatives, for example:

Papaverine(1- (3,4-dimethoxyphenyl)methyl-6,7-dimethoxyisoquinoline) and salts thereof; and 6,7-Diethoxy-1-(4,5-diethoxybenzyl)isoquinoline or its salts e.g. its hydrochloride;

(c) Derivatives of pyrimido(5,4-d)pyrimidine, for example:

Dipyridamole(2,2',2'',2'''-(4,8-dipiperidinopyrimido[5,4-d]pyrimidin-2,6-diyldinitrilo)tetraethanol) and its salts;

2,2',2'',2'''-[[4-(1-piperidinyl)pyrimido[5,4-d]pyrimidin-2,6-diyl]dinitrilo]tetrakisethanol and its salts; and 2,4,6-tri-4-morpholinylpyrimido[5,4-d]pyrimidine and its salts.

(d) Derivatives of thieno[3,2-d]pyrimidine, for example:

N-[4-(4-morpholinyl)thieno[3,2-d]pyrimidin-2-yl]-1,2-ethanediamine.

(e) Derivatives of pyrazolo[3',4':2,3]pyrido[4,5-b][1,5]benzodiazepin-6-(3H)-one, for example:

3-Ethyl-7,12-dihydro-7,12-dimethylpyrazolo[4,',3':5,6-]pyrido[4,3-b]-[1,5]benzodiazepin-6-(3H)-one;
3-Ethyl-7,12-dihydro-9-methoxy-7,12-dimethyl-pyrazolo[3',4':2,3]pyrido[4,5-b][1,5]benzodiazepin-6-(3H)-one; and
10-Chloro-3-ethyl-7,12-dimethyl-7,12-dihydropyrazolo[4',3':5,6]pyrido[4,3-b][1,5]benzodiazepin-6-(3H)-one.

(f) Derivatives of 1H- or 2H-pyrazolo[3,4-b]pyridine, for example:

4-(Butylamino)-1-ethyl-1H-pyrazolo[3,4]pyridine-5-carboxylic acid ethyl ester;
4-(Butylamino)-1H-pyrazolo[3,4-b]pyridine-6-carboxylic acid ethyl ester;
4-Chloro-1-ethyl-3-methyl-1H-pyrazolo[3,4-b]pyridine-5-acetonitrile;
1-Ethyl-4-(isopropylidenehydrazine)-3-methyl-1H-pyrazolo[3,4-b]pyridine-5-carboxylic acid ethyl ester or its salts such as its hydrochloride hemihydrate; and
2-Methyl-6-phenyl-4-(1-piperidinyl)-2H-pyrazolo[3,4-b]pyridine or its salts e.g. its hydrochloride.

(g) Derivatives of 5H-furo-[3,4-e]pyrazolo[3,4-b]pyridine-5-one, for example:

4-(Butylamino)-1-ethyl-1,7-dihydro-7-hydroxy-5H-furo-[3,4-e]pyrazolo[3,4-b]pyridine-5-one; and
(h) Derivatives of 1(2H)-naphthalenone, for example:

2[(Dimethylamino)methyl]-3,4-dihydro-7-methoxy-1(2H)-naphthalenone or its salts e.g. its 1:1 hydrochloride.

The active compounds are particularly useful in the treatment and/or prophylaxis of thrombo-embolic disorders in mammals, including man. It is to be understood that the term "thrombo-embolic disorder" includes those disorders whose etiology is associated with platelet aggregation.

The active compounds are useful wherever it is desired to inhibit platelet aggregation and/or to reduce the adhesive character of platelets, and consequently to treat or prevent the formation of thrombi in mammals, including man. For example, the compounds are useful in the treatment and prevention of myocardial infarcts, cerebro-vascular thrombosis and ischaemic peripheral vascular disease; to treat and prevent post-operative thrombosis; and to promote patency of vascular grafts following surgery.

The active compounds are also useful as an addition to blood, blood products, blood substitutes, and other fluids which are used in artificial extra-corporeal circulation and perfusion of isolated body portions, e.g., limbs and organs, whether attached to the original body, detached and being preserved or prepared for transplant, or attached to a new body. It may also be used in laboratory animals, e.g. cats, dogs, rabbits, monkeys and rats, for these purposes in order to develop new methods and techniques for organ and limb transplants.

The active compounds also exhibit some vasodilatory action on blood vessels and therefore have a utility as anti-hypertensives for the treatment of high blood pressure in mammals, including man.

The active compounds may also be used in the prevention, treatment or prophylaxis of angina pectoris and in the prevention or delay of the onset of shock.

The amount of active compound required for therapeutic or prophylactic effect will vary with the route of administration, and the nature of the condition under treatment. In general a suitable dose for a mammal, including man, of active compound will lie in the range of 0.1 to 300 mg per kg body weight, particularly from 0.5 to 10 mg per kg body weight, for example 2 mg per kg. A suitable single oral dose for an adult human lies within the range of 50 to 600 mg, for example 150 mg, given say three times a day.

While it is possible for an active compound to be administered as the raw chemical it is preferable to present it as a pharmaceutical formulation. The formulations, both for veterinary and for human medical use, of the present invention comprise an active compound as above defined, together with one or more acceptable carriers thereof and optionally other therapeutic ingredients. The carrier(s) must be 'acceptable' in the sense of being compatible with the other ingredients of the formulation and not deleterious to the recipient thereof. Unit doses of a formulation may contain between 60 mg and 1.5 g of an active compound.

The formulations include those suitable for oral, rectal, vaginal or parenteral (including subcutaneous, intramuscular and intravenous) administration. Preferred formulations include tablets, capsules and injectable suspensions or solutions.

The formulations may conveniently be presented in unit dosage form and may be prepared by any of the methods well known in the art of pharmacy. All methods include the step of bringing into association the active compound (in the form of the base or a pharmaceutically acceptable acid addition salt) with the carrier, which constitutes one or more accessory ingredients. In general the formulations are prepared by uniformly and intimately bringing into association the active compound with liquid carrier(s) or finely divided solid carrier(s) or both, and then, if necessary, shaping the product into the desired formulation.

It will be appreciated from the fore-going that this invention provides the following features:

(a) Novel 1-substituted imidazoles of formula (I) and acid addition salts thereof.

(b) Methods of preparing imidazoles of formula (I) and acid addition salts thereof.

(c) Pharmaceutical formulations containing an imidazole of formula (I) or a pharmaceutically acceptable acid addition salt thereof and a pharmaceutically acceptable carrier.

(d) Method of preparing the pharmaceutical formulations containing an imidazole of formula (I) or a pharmaceutically acceptable acid addition salt thereof.

(e) A method for the treatment or prophylaxis of a thrombo-embolic disorder in a mammal or mammalian tissue, including man or human tissue, comprising administering an effective amount of an active compound.

(f) A method of prevention, treatment or prophylaxis of angina pectoris in a mammal, including man, which comprises administering to the mammal, an effective amount of an imidazole of formula (I) or a pharmaceutically acceptable acid addition salt thereof.

(g) A method of preventing or delaying the onset of shock in a mammal, including man, which comprises administering to the mammal an effective amount of an imidazole of formula (I) or a pharmaceutically acceptable addition salt thereof.

The following Examples are provided by way of an illustration of the present invention and should in no way be construed as constituting a limitation thereof. All temperatures are given in degrees Celsius.

EXAMPLE 1

Preparation of 1-(3,4-Dimethylbenzyl)imidazole

1-Chloromethyl-3,4-dimethylbenzene (34.76 g, 0.225 mol) was added to a mixture of imidazole (13.6 g, 0.2 mol) and sodium bicarbonate (16.8 g, 0.2 mol) in dry methanol (100 ml). Following the addition, the reaction mixture was stirred and heated under reflux for 3 hours (h).

After cooling, the reaction mixture was filtered, and the filtrate was evaporated under reduced pressure to afford a yellow oil. The residue was extracted with chloroform (3×100 ml), and the combined extracts were washed with saturated brine (100 ml). The chloroform solution was dried over magnesium sulphate, and then concentrated under reduced pressure. The resulting oil was purified using a silica gel column and ethyl acetate/methanol (9:1) as eluent. The product fractions were pooled, concentrated, and the resulting oil was distilled to afford 1-(3,4-dimethylbenzyl)imidazole, b.p. 128°–130°/0.3 mm Hg.

EXAMPLE 2

Salts of 1-(3,4-Dimethylbenzyl)imidazole

A. Hydrogen Fumarate

A solution of fumaric acid (0.29 g, 0.0025 mol) in hot ethanol (10 ml) was added to a stirred solution of 1-(3,4-dimethylbenzyl)imidazole (0.46 g, 0.0025 mol) in hot ethanol (10 ml). After boiling for 0.25 h, the solution was evaporated to afford a white solid. Recrystallisation of the solid from ethyl acetate afforded 1-(3,4-dimethylbenzyl)imidazole hydrogen fumarate 1/6 hydrate as a white solid m.p. 138°–140°.

B. Hydrogen Succinate

A hot solution of succinic acid (0.295 g, 0.0025 mol) in ethanol (20 ml) was added to a stirred, hot solution of 1-(3,4-dimethylbenzyl)imidazole (0.46 g, 0.0025 mol) in hot ethanol (10 ml). After boiling for 0.25 h, the solution was evaporated under reduced pressure to afford a white solid. Recrystallisation of the solid from ethyl acetate/petroleum ether (b.p. 40°–60°) afforded 1-(3,4-dimethylbenzyl)imidazole hydrogen succinate as white crystals, m.p. 134°–135°

C. Hydrogen Oxalate

A hot solution of oxalic acid (0.225 g, 0.0025 mol) in dry ethanol (10 ml) was added to a solution of 1-(3,4-dimethylbenzyl)imidazole (0.46 g, 0.0025 mol) in hot ethanol (20 ml). After boiling for 0.25 h, the solution was evaporated to afford a white solid. Recrystallisation of the solid from ethanol/petroleum ether (b.p. 40°–60°) afforded 1-(3,4-dimethylbenzyl)imidazole hydrogen oxalate as a white solid, m.p. 92°–93°.

EXAMPLE 3

Preparation of 1-[3-(2,4-Dichlorophenyl)prop-2-enyl]imidazole

1-Chloro-3-(2,4-dichlorophenyl)prop-2-ene (11.1 g, 0.05 mol) was added dropwise to a stirred solution of imidazole (3.4 g, 0.05 mol) and potassium tert-butoxide (5.6 g, 0.05 mol) in butan-1-ol (100 ml) Following the addition, the reaction mixture was stirred and heated under reflux for 3.5 h.

After cooling, the reaction mixture was filtered, and the filtrate was concentrated under reduced pressure. Hydrochloric acid (150 ml, 2 M) was then added to the residue and the aqueous mixture was washed with ether (1×60 ml). The acidic solution was then basified with sodium hydroxide solution (10 M), and the resulting oil was extracted with chloroform. The chloroform extracts were combined and dried over magnesium sulphate. Evaporation of the chloroform under reduced pressure afforded a pale yellow oil which was purified using a silica gel column and by elution with ethyl acetate/methanol (9:1). The product fractions were pooled and concentrated to afford an oil which was distilled, to afford 1-[3-(2,4-dichlorophenyl)prop-2-enyl]imidazole, b.p. 144°–148°/0.007 mmHg.

EXAMPLE 4

Preparation of 1-[3-(2,6-Dichlorophenyl)prop-2-enyl]imidazole

1-Chloro-3-(2,6-dichlorophenyl)prop-2-ene (11.1 g, 0.05 mol) was added dropwise to a stirred solution of imidazole (3.4 g, 0.05 mol) and potassium tert-butoxide (5.6 g, 0.05 mol) in butan-1-ol (100 ml) Following the addition, the reaction mixture was stirred and heated under reflux for 3.5 h.

After cooling, the reaction mixture was filtered, and the filtrate was concentrated under reduced pressure. Hydrochloric acid (150 ml, 2 M) was then added to the residue, and the aqueous mixture was washed with ether (1×60 ml). The acidic solution was then basified with sodium hydroxide solution (10 M), and the resulting oil was extracted with chloroform. The chloroform extracts were combined and dried over magnesium sulphate. Evaporation of the chloroform under reduced pressure afforded a pale yellow oil which was purified using a silica gel column and by elution with ethyl acetate/methanol (9:1). The product fractions were pooled and concentrated to afford an oil which was distilled, to afford 1-[3-(2,6-dichlorophenyl)prop-2-enyl]imidazole, b.p. 156°–158°/0.02 mmHg.

EXAMPLE 5

Preparation of 1-[3-(2,4-Dichlorophenyl)propyl]imidazole 1-(3-Chloropropyl)-2,4-dichlorobenzene (16.65 g, 0.075 mol) was added dropwise to a stirred solution of imidazole (5.1 g, 0.075 mol) and potassium tert-butoxide (8.4 g, 0.075 mol) in dry butan-1-ol. Following the addition, the reaction mixture was stirred and heated under reflux for 2 h.

After cooling, the reaction mixture was filtered and the filtrate was concentrated under reduced pressure. The residue was dissolved in hydrochloric acid (150 ml, 2 M) and the solution was washed with ether (1×50 ml). The acid solution was then basified with sodium hydroxide solution 10 M), and the basic solution was extracted with chloroform (3×50 ml). The combined chloroform extracts were dried over magnesium sulphate and were then concentrated under reduced pressure. The resulting oil was purified using a silica gel column, and elution with ethyl acetate/methanol (9:1). The product fractions were pooled, concentrated, and the resulting oil was distilled to afford 1-[3-(2,4-dichlorophenyl)propyl]imidazole, b.p. 140°/0.04 mm Hg.

EXAMPLE 6

By the method described in Example 1 above the following compounds were prepared:

(a) 1-(2,4,6-trimethylbenzyl)imidazole, B.p. 104°–108°/0.005 mm Hg;
(b) 1-(3-(3,4,5-trimethoxyphenyl)prop-2-enyl)imidazole;
(c) 1-(3-(3,4-dimethoxyphenyl)prop-2-enyl)imidazole;
(d) 1-(3-(2-hydroxyphenyl)prop-2-enyl)imidazole;
(e) 1-(3-(3-bromophenyl)prop-2-enyl)imidazole;
(f) 1-(3-(4-chlorophenyl)prop-2-enyl)imidazole;
(g) 1-(3-(3,4-dimethylphenyl)prop-2-enyl)imidazole;
(h) 1-(3-(2-methoxyphenyl)prop-2-enyl)imidazole.

EXAMPLE 7

Biological Results

Horse platelets were prepared from whole horse blood by differential centrifugation. Approximately $10^6$ platelets were homogenised in 1 ml 100 mM Tris buffer pH 7.4. Various concentrations of active compound were added and the reaction sets incubated for 5 minutes at ambient temperature. To each tube was added 20 nM of arachidonic acid containing $10^6$ DPM of labelled arachidonic acid and the tubes incubated for 3 minutes at 37° C. in a shaking water bath. After incubation the radioactive products were extracted from the acidified aqueous phase with ethyl acetate and after concentration resolved by thin layer chromatography on silica gel with chloroform/methanol/acetic acid/water (90:8:1:0.8) as a developing solvent. The amount of thromboxane produced was measured by scraping off the radioactive zone corresponding to thromboxane $B_2$ and estimating the radioactivity in a liquid scintillation counter.

The concentration of active compound to reduce the enzyme activity by 50% ($ED_{50}$) was established. The results are shown in Table A The selectivity of the active compounds was measured in a similar manner to that described above and the amount of PGE, PGF and PGD produced was determined. The greater the selectivity, the more of the anti-aggregating prostaglandins are produced.

The $ED_{50}$ and Selectivity results are shown in Table A in which 0 indicates no selectivity; + low selectivity: + + medium selectivity; + + + high selectivity, and + + + + exceptionally high selectivity.

TABLE A

| Compound | $ED_{50}$ µg/ml | Selectivity |
| --- | --- | --- |
| 1-(3,4-Dimethylbenzyl)imidazole | 6 | ++ |
| 1-(3-(2,4-Dichlorophenyl)prop-2-enyl)imidazole | 4.1 | + |
| 1-(3-(2,6-Dichlorophenyl)prop-2-enyl)imidazole | 1 | + |
| 1-(2,4,6-Trimethylbenzyl)imidazole | 3.4 | ++ |
| 1-3-(2,4-Dichlorophenyl)propyl imidazole | 0.5 | ++ |

EXAMPLE 8

| | |
| --- | --- |
| 1-(3,4-Dimethylbenzyl)imidazole (as a salt) | 150 mg |
| Starch | 25 mg |
| Polyvinylpyrrolidone | 2 mg |
| Magnesium stearate | 3 mg |

The imidazole salt is ground to a fine powder, blended with the starch and then the mixture granulated with an aqueous solution of the polyvinylpyrrolidone. The granules are sieved 1000µ, dried, sieved again and the magnesium stearate added. The mixture is then compressed into tablets.

In the same manner, tablets of 1-(3-(2,4-dichlorophenyl)prop-2-enyl)imidazole, 1-(3-(2,6-dichlorophenyl)prop-2-enyl)imidazole, 1-(2,4,6-trimethylbenzyl)imidazole and 1-(3-(2,4-dichlorophenyl)propyl)imidazole are prepared.

EXAMPLE 9

Tablet formulation

Tablets (150 mg) of the imidazoles described in the preceding Example 8 are prepared in the same manner from the following ingredients:

| | |
| --- | --- |
| The Imidazole Compound (as a salt) | 150 mg |
| Lactose | 100 mg |
| Starch | 30 mg |
| Polyvinylpyrrolidone | 2 mg |
| Magnesium stearate | 3 mg |

In the preparation, the lactose is blended with the starch.

EXAMPLE 10

Tablet Formulation

Tablets (100 mg of the imidazoles of Example 8 are prepared in the same manner from the following ingredients:

| | |
| --- | --- |
| The Imidazole Compound (as a salt) | 100 mg |
| Sodium starch glycollate | 10 mg |
| Polyvinylpyrrolidone | 2 mg |
| Magnesium stearate | 3 mg |

EXAMPLE 11

Tablet formulation

Tablets (150 mg) of the imidazoles of Example 8 are prepared in the same manner from the following ingredients, except that the starch, pregelled starch and imidazole compound are all blended together prior to granulation:

| | |
| --- | --- |
| The Imidazole Compound (as a salt) | 150 mg |
| Starch | 25 mg |
| Pregelled starch | 5 mg |
| Magnesium stearate | 3 mg |

EXAMPLE 12

Injectable formulation

| | |
| --- | --- |
| Imidazole Compound of formula (I) | 15.0 g |
| Lactic Acid B.P. | q.s. to pH 3.0 |
| Water for Injections B.P. | to 100.0 ml |

Suspend the compound in ¾ of the available quantity of water. Add sufficient lactic acid to dissolve the compound and to reduce the pH to 3.0. Dilute to volume with Water for Injections.

Sterilise the solution by passage through a membrane filter, pore size 0.22 μm.

Distribute the solution using aseptic precautions into sterilised ampoules, 1 ml per ampoule. Seal by fusion of the glass.

Each 1 ml ampoule supplies 150 mg of the imidazole compound: 1(3,4-dimethylbenzyl)imidazole hydrogen fumarate.

EXAMPLE 13

Injectable formulation

| | |
|---|---|
| Imidazole Compound of formula (I) | 15.0 g |
| Citric Acid B.P. | q.s. to pH 3.0 |
| Chlorocresol | 0.1 g |
| Water for Injections to | 100.0 ml |

Suspend the compound in ½ the final volume of Water for Injections. Add sufficient citric acid as a 10% solution in Water for Injections to dissolve the compound and reduce the pH to 3.0. Dilute to volume with Water for Injections.

Sterilise the solution by passage through a membrane filter, pore size 0.22 μm.

Distribute the solution with aseptic precautions into sterilised vials, 25 ml per vial. Stopper with sterile rubber closures and seal with an aluminium cap.

Each 1 ml of solution provides 150 mg of the compound: 1-(3,4-dimethylbenzyl)imidazole hydrogen fumarate.

EXAMPLE 14

Injectable formulation

In the manner described in the preceding two Examples, injectable formulations of 1-(3-(2,4-dichlorophenyl)prop-2-enyl)imidazole, 1-(3-(2,6-dichlorophenyl)prop-2-enyl)imidazole, 1(2,4,6-trimethylbenzyl)imidazole, and 1-(3-(2,4-dichlorophenyl)propyl)imidazole salts were prepared.

EXAMPLE 15

Preparation of 1-(2-Phenylethyl)imidazole (2-Bromoethyl)benzene (41.62 g, 0.225 mol) was added dropwise to a stirred mixture of imidazole (13.6 g, 0.2 mol) and sodium bicarbonate (16.8 g, 0.2 mol) in methanol (100 ml). Following the addition, the reaction mixture was stirred at ambient temperature for 24 h, and then stirred and heated under reflux for 6 h. After concentration of the reaction mixture under reduced pressure, the residue was treated with water (100 ml), and this mixture was extracted with chloroform (3×75 ml). The combined extracts were dried (magnesium sulphate), and the solution was then evaporated under reduced pressure. The resulting brown oil was distilled to afford 1-(2-phenylethyl)imidazole, b.p. 122°/0.2 mmHg. The slightly impure product was purified using a silica gel column and by elution with ethyl acetate/methanol (9:1). The product fractions were pooled, concentrated, under reduced pressure, and then distilled, to afford the pure product, b.p. 110°/0.1 mmHg.

EXAMPLE 16

Preparation of 1-(3-Phenylpropyl)imidazole (3-Bromophenyl)benzene (9.95 g, 0.05 mol) was added to a stirred mixture of imidazole (3.4 g, 0.05 mol) and sodium bicarbonate (4.2 g, 0.05 mol) in methanol (100 ml). Following the addition, the reaction mixture was stirred and heated under reflux for 15 h.

After cooling, the reaction mixture was filtered, and the filtrate was concentrated under reduced pressure. The residue was treated with water (110 ml) and with hydrochloric acid (1×150 ml, 2 M) and the resulting mixture was extracted with ether (1×70 ml). The acid solution was basified with sodium hydroxide solution (10 M) and the resulting oil was extracted with chloroform (3×120 ml). The chloroform extracts were combined and dried over magnesium sulphate. The chloroform solution was then concentrated under reduced pressure to afford a brown oil which was purified using silica gel column and by elution with ethyl acetate/methanol (9:1). The product fractions were pooled, concentrated, and the resulting oil was distilled, to afford 1-(3-phenylpropyl)imidazole, b.p. 126°/0.15 mmHg.

EXAMPLE 17

Preparation of 1-(3-Phenylprop-2-enyl)imidazole

1-Chloro-3-phenylprop-2-ene (25.0 g, 0.164 mol) was added dropwise to a stirred mixture of imidazole (11.5 g, 0.169 mol) and sodium bicarbonate (13.75 g, 0.164 mol) in methanol (100 ml). Following the addition, the reaction mixture was stirred and heated under reflux for 14 h.

After cooling, the reaction mixture was filtered, and the filtrate was then concentrated under reduced pressure. The residue was treated with water (150 ml), and the aqueous mixture was then extracted with chloroform (3×100 ml). The chloroform extracts were then combined and dried over magnesium sulphate. Evaporation of the chloroform under reduced pressure afforded a brown oil which was purified using a column of silica gel and by elution with ethyl acetate/methanol (9:1). The product fractions were pooled and the solution concentrated to afford a pale yellow oil which was distilled, to afford 1-(3-phenylprop-2-enyl)imidazole, b.p. 150°/152°/0.2 mm Hg. The product solidified on cooling, and was recrystallised from toluene to afford a pale yellow crystalline solid, m.p. 37°-38°.

EXAMPLE 18

Preparation of 1-(2-Phenylpropyl)imidazole

1-Bromo-2-phenylpropane (44.78 g, 0.225 mol) was added dropwise to a stirred boiling solution of imidazole (13.6 g, 0.2 mol) in ethanolic sodium ethoxide [prepared from sodium (5.5 g, 0.24 mol) and dry ethyl alcohol (100 ml]. Following the addition, the reaction mixture was stirred and heated under reflux for 20 h.

After cooling, the reaction mixture was filtered, and the filtrate was concentrated under reduced pressure. The residue was poured onto hydrochloric acid (100 ml, 6 M), and the aqueous layer was separated, washed with ether (1×70 ml), and was then basified with sodium hydroxide solution (10 M). The resulting oil was extracted with ether (2×100 ml), and the ether extracts were combined and dried over magnesium sulphate. The ether solution was concentrated to afford a brown oil which was purified using a silica gel column and by elution with ethyl acetate/methanol (9:1). The product fractions were pooled, concentrated, and the resulting oil was distilled, to afford 1-(2-phenylpropyl)imidazole, b.p. 100°-102°/0.02 mmHg.

EXAMPLE 19

Preparation of 1-Benzylimidazole

1-Chloromethylbenzene (6.33 g, 0.05 mol) was added dropwise to a stirred, boiling mixture of imidazole (3.4 g, 0.05 mol) and sodium bicarbonate (4.2 g, 0.05 mol) in dry ethanol (100 ml). Following the addition, the reaction mixture was stirred and boiled for 20 h.

After cooling, the reaction mixture was evaporated under reduced pressure. The residue was treated with water (1×100 ml), and the mixture was washed with ether (3×70 ml). The ether extracts were combined and dried over magnesium sulphate. Concentration of the ether solution under reduced pressure afforded an oil which was purified using a silica gel column, and by elution with ethyl acetate/methanol (9:1). The product fractions were pooled and concentrated to afford a solid which was recrystallised from aqueous ethanol to afford 1-benzylimidazole, m.p. 71°–72°.

EXAMPLE 20

Preparation of 1-Benzylimidazole

A. N-Benzylaminoacetaldehyde Diethyl Acetal

A stirred mixture of chloroacetaldehyde diethyl acetal (50 g, 0.328 mol), and benzylamine (150.0 g, 1.4 mol) was heated at 130° for 3 h. The mixture was then left at ambient temperature overnight. Next day, water (150 ml) was added, and the resulting solution was basified with sodium hydroxide solution (25 ml, 10 M). The mixture was then extracted with ether (2×100 ml), and the extracts were combined and dried over magnesium sulphate. Evaporation of the ether under reduced pressure afforded a brown oil which was distilled to afford N-benzylaminoacetaldehyde diethyl acetal, b.p. 148°–150°/20 mmHg.

B. 1-Benzyl-2-thioimidazole

To a mixture of N-benzylaminoacetaldehyde diethyl acetal (19.0 g, 0.085 mol) and sodium thiocyanate (8.9 g, 0.11 mol) in aqueous ethanol (50 ml, 50%) was added hydrochloric acid (10 ml, 12 M). The mixture was then heated on a steam bath for 3 h in an open flask, and the residue was then dissolved in sodium hydroxide solution (250 ml, 2 M) and the reaction mixture was then boiled with charcoal and filtered. The filtrate was acidified with hydrochloric acid (12 M), and the resulting precipitate was separated. Recrystallisation from ethyl acetate afforded 1-benzyl-2-thioimidazole, m.p. 150°–151°.

C. 1-Benzylimidazole

1-Benzyl-2-thioimidazole (5.0 g, 0.0263 mol) was added portionwise to a stirred solution of concentrated nitric acid (6.1 ml) in water (15.2 ml) at 35°–40°. Following the addition the reaction mixture was stirred for 1 h, and then treated with sodium hydroxide solution (11 ml, 10 M). The resulting mixture was extracted with chloroform (3×100 ml) and the combined extracts were dried over magnesium sulphate. Concentration of the chloroform solution afforded a brown oil which was distilled in vacuo to afford 1-benzylimidazole as a colourless solid, b.p. 186°–188°/25 mm. Recrystallisation from petroleum ether (b.p. 60°–80°) afforded the product as colourless needles, m.p. 73°–74°.

EXAMPLE 21

Preparation of 1-(3-Nitrobenzyl)imidazole

1-Chloromethyl-3-nitrobenzene (48.6 g, 0.283 mol) was added to a mixture of imidazole (13.6 g, 0.2 mol) and sodium bicarbonate (16.8 g, 0.2 mol) in methanol (100 ml). Following the addition, the reaction mixture was stirred and heated under reflux for 4 h.

After cooling, the reaction mixture was concentrated under reduced pressure. The residue was dissolved in water (100 ml), and this solution was extracted with chloroform (3×100 ml).

The chloroform extracts were dried over magnesium sulphate and then concentrated under reduced pressure to afford a yellow oil. The oil was purified using a silica gel column and using ethyl acetate/methanol (9:1) as eluent. The product fractions were pooled and concentrated under reduced pressure to afford a solid, which was recrystallised from petroleum ether (b.p. 80°–100°) to afford 1-(3-nitrobenzyl)imidazole as faint yellow needles, m.p. 97°–98°.

EXAMPLE 22

Preparation of 1-(3-Aminobenzyl)imidazole

A mixture of 1-(3-nitrobenzyl)imidazole (0.5 g, 0.0025 mol) and palladium on charcoal (0.05 g, 10%) in dry ethanol (20 ml) was stirred under an atmosphere of hydrogen for 0.25 h. The reaction mixture was then filtered through Hyflo-supercel, and the ethanol was evaporated under reduced pressure to give a colourless oil. The oil was distilled to yield 1-(3-aminobenzyl)imidazole, b.p. 160°/0.01 mm Hg, which solidified on cooling. Recrystallisation of the solid from toluene gave the product as a white solid, m.p. 75°–76°.

EXAMPLE 23

Preparation of 1-(2,4-Dichlorobenzyl)imidazole

1-Chloromethyl-2,4-dichlorobenzene (44.0 g, 0.225 mol) was added to a mixture of imidazole (13.6 g, 0.2 mol) and sodium bicarbonate (16.8 g, 0.2 mol) in methanol (100 ml). Following the addition, the reaction mixture was stirred and boiled for 3.5 h.

After cooling the reaction mixture was concentrated under reduced pressure, and water (100 ml) was then added. The aqueous solution was extracted with chloroform (3×100 ml) and the chloroform extracts were combined, washed with saturated brine (100 ml), and the dried (magnesium sulphate). Evaporation of the chloroform solution under reduced pressure afforded a pale yellow oil, which was purified using a silica gel column and ethyl acetate/methanol (9:1) as eluent. The product fractions were combined, concentrated, and the resulting oil was distilled to afford 1-(2,4-dichlorobenzyl)imidazole, b.p. 128°–130°/0.005 mm Hg. The product solidified on standing, and was recrystallised from petroleum ether (b.p. 40°–60°), to afford the product as a colourless solid, m.p. 49°50°.

EXAMPLE 24

Preparation of 1-(4-Fluorobenzyl)imidazole

1-Chloromethyl-4-fluorobenzene (32.51 g, 0.225 mol) was added dropwise to a stirred mixture of imidazole (13.6 g, 0.2 mol) and sodium bicarbonate (16.8 g, 0.2 mol) in methanol (100 ml). Following the addition, the reaction mixture was stirred and heated under reflux for 2 h.

After cooling, the reaction mixture was concentrated under reduced pressure, and the residue was dissolved in water (100 ml) and the aqueous solution was extracted with chloroform (3×100 ml). The chloroform extracts were combined, washed with saturated brine (100 ml) and then dried (magnesium sulphate). Concentration of the chloroform solution under reduced pressure afforded a yellow oil which was purified using a silica gel column and elution with ethyl acetate/methanol (9:1). The product fractions were pooled, concentrated, and the resulting oil was distilled to afford 1-(4-fluorobenzyl)imidazole, b.p. 94°–97°/0.18 mm Hg.

EXAMPLE 25

Preparation of 1-(4-Methylbenzyl)imidazole

1-Chloromethyl-4-methylbenzene (31.64 g, 0.225 mol) was added dropwise to a stirred mixture of imidazole (13.6 g, 0.2 mol) and sodium bicarbonate (16.8 g, 0.2 mol) in methanol (100 ml). Following the addition, the reaction mixture was stirred and heated under reflux for 2 h.

After cooling, the reaction mixture was concentrated under reduced pressure. The residue was then dissolved in water (100 ml) and the aqueous solution was extracted with chloroform (3×100 ml). The chloroform extracts were combined, washed with saturated brine (100 ml) and then dried (magnesium sulphate). Concentration of the chloroform solution under reduced pressure afforded a yellow oil which was purified using a silica gel column and elution with ethyl acetate/methanol (9:1). The product fractions were pooled, concentrated, and the resulting oil was distilled to afford 1-(4-methylbenzyl)imidazole, b.p. 110°–114°/0.2 mm Hg, which solidified on standing. Recrystallisation from ethyl acetate/petroleum ether (b.p. 40°–60°) afforded the product as a colourless solid, m.p. 51°–53°.

EXAMPLE 26

Preparation of 1-(2-Bromobenzyl)imidazole

1-Bromo-2-bromomethylbenzene (12.5 g, 0.05 mol) was added dropwise to a stirred, boiling mixture of imidazole (3.4 g, 0.05 mol) and potassium tert-butoxide (5.6 g, 0.05 mol) in dry butan-1-ol (80 ml). Following the addition, the reaction mixture was stirred and boiled for 2.5 h.

After cooling, the reaction mixture was filtered and the filtrate was evaporated under reduced pressure. The residue was dissolved in hydrochloric acid (150 ml, 2 M), and the acid solution was washed with ether (2×50 ml). The acid solution was basified with sodium hydroxide solution (10 M), and the basic solution was extracted with chloroform (4×50 ml), and the chloroform extracts were combined and dried (magnesium sulphate). Concentration of the chloroform solution under reduced pressure afforded a brown oil which was purified using a silica gel column and elution with ethyl acetate/methanol (9:1). The product fractions were combined, concentrated, and distilled to afford 1-(2-bromobenzyl)imidazole, b.p. 128°/0.05 mm.

EXAMPLE 27

Preparation of 1-(4-Bromobenzyl)imidazole

1-Bromo-4-bromomethylbenzene (12.5 g, 0.05 mol) was added dropwise to a stirred, boiling mixture of imidazole (3.4 g, 0.05 mol) and potassium tert-butoxide (5.6 g, 0.05 mol) in dry butan-1-ol (60 ml). Following the addition the reaction mixture was stirred and boiled for 4 h.

After cooling, the reaction mixture was filtered and the filtrate was evaporated under reduced pressure. The residue was dissolved in hydrochloric acid (150 ml, 2 M), and the acid solution was washed with ether (2×50 ml). The acid solution was basified with sodium hydroxide solution (10 M), and the basic solution was extracted with chloroform (4×50 ml), and the chloroform extracts were combined and dried (magnesium sulphate). Concentration of the chloroform solution under reduced pressure afforded a brown oil which was purified using a silica gel column and elution with ethyl acetate/methanol (9:1). The product fractions were combined, concentrated, and distilled to afford 1-(4-bromobenzyl)imidazole, b.p. 122°–126°/0.03 mm Hg.

The oil solidified on standing and was recrystallised from ethyl acetate/petroleum ether (b.p. 60°–80°) to afford the product as white striated needles, m.p. 81°–83°.

EXAMPLE 28

Preparation of 1-(3-Bromobenzyl)imidazole

1-Bromo-3-bromomethylbenzene (12.5 g, 0.05 mol) was added dropwise to a stirred, boiling mixture of imidazole (3.4 g, 0.05 mol) and potassium tert-butoxide (5.6 g, 0.05 mol) in dry butan-1-ol (80 ml). Following the addition, the reaction mixture was stirred and boiled for 4 h.

After cooling, the reaction mixture was filtered and the filtrate was evaporated under reduced pressure. The residue was dissolved in hydrochloric acid (150 ml, 2 M), and the acid solution was washed with ether (2×50 ml). The acid solution was basified with sodium hydroxide solution (10 M), and the basic solution was extracted with chloroform (4×50 ml) and the chloroform extracts were combined and dried (magnesium sulphate). Concentration of the chloroform solution under reduced pressure afforded a brown oil which was purified using a silica gel column and elution with ethyl acetate/methanol (9:1). The product fractions were combined, concentrated, and distilled to afford 1-(3-bromobenzyl)imidazole, b.p. 124°–126°/0.06 mm Hg.

EXAMPLE 29

Preparation of 1-(4-i-Propylbenzyl)imidazole

1-Chloromethyl-4-i-propylbenzene (16.85 g, 0.1 mol) was added dropwise to a stirred solution of imidazole (6.8 g, 0.1 mol) and potassium tert-butoxide (11.2 g, 0.1 mol) in dry butan-1-ol (100 ml). Following the addition, the reaction mixture was stirred and heated under reflux for 4 h.

After cooling, the reaction mixture was filtered and the filtrate was concentrated under reduced pressure. Hydrochloric acid (150 ml, 2 M) was added to the residue, and the acid mixture was washed with ether (2×70 ml). The acid solution was then basified with sodium hydroxide solution (10 M), and the resulting oil was extracted with chloroform (3×100 ml). The chloroform extracts were combined, dried (magnesium sulphate), and then concentrated under reduced pressure to afford an oil which was purified using a silica gel column and elution with ethyl acetate/methanol (9:1). The product fractions were pooled and concentrated under reduced pressure to afford a pale yellow oil. Distillation of the oil in vacuo gave 1-(4-i-propylbenzyl)imidazole as a colourless oil, b.p. 112°–114°/0.08 mm Hg.

EXAMPLE 30

Preparation of 1(2-Chlorobenzyl)imidazole

A solution of imidazole (3,4 g, 0.05 mol), 2-chlorobenzyl bromide (10.28 g, 0.05 mol) and potassium tert-butoxide (5.6 g, 0.05 mol) in dry butan-1-ol (100 ml) was stirred and heated under reflux for 4 h.

After cooling, the reaction mixture was filtered, and the filtrate was concentrated under reduced pressure to afford a brown residue. The residue was dissolved in hydrochloric acid (150 ml), and the acid solution was washed with ether (100 ml). The acid solution was then basified with sodium hydroxide solution (10 M), and the product was extracted with chloroform (3×50 ml). The combined chloroform extracts were dried (MgSO$_4$) and then concentrated under reduced pressure to afford a brown oil. The oil was purified using a silica gel column and by elution with chloroform/methanol (9:1). The product fractions were pooled and concentrated to afford an oil which was distilled, to give 1-(2-chlorobenzyl)imidazole as a colourless oil, b.p. 114°–116°/0.25 mm Hg.

EXAMPLE 31

Preparation of Salts of 1-(2-Bromobenzyl)imidazole (a) Hydrogen Fumarate

A solution of fumaric acid (0.18 g) in hot ethanol (10 ml) was added to a solution of 1-(2-bromobenzyl)imidazole (0.4 g) in hot ethanol (5 ml). After boiling for 10 minutes, the solution was evaporated under reduced pressure to afford a white solid. Recrystallisation of the solid from propan-2-ol gave 1-(2-bromobenzyl)imidazole hydrogen fumarate, m.p. 158°–159°.

(b) Hydrogen Succinate

A solution of succinic acid (0.19 g) was dissolved in hot ethanol (10 ml) was added to a solution of 1-(2-bromobenzyl)imidazole (0.4 g) in hot ethanol (5 ml). After boiling for 10 minutes, the solution was evaporated under reduced pressure to afford a white solid. Recrystallisation of the solid from ethyl acetate/light petroleum gave 1-(2-bromobenzyl)imidazole hydrogen succinate, m.p. 112°–113°.

(c) Hydrogen Oxalate

A solution of oxalic acid (0.14 g) in hot ethanol (10 ml) was added to a solution of 1-(2-bromobenzyl)imidazole (0.4 g) in hot ethanol (5 ml). After boiling for 10 minutes, the solution was evaporated under reduced pressure to afford a white solid. Recrystallisation of the solid from propan-2-ol gave 1-(2-bromobenzyl)imidazole hydrogen oxalate, m.p. 146°–147°.

EXAMPLE 32

Biological Results

By the method of Biological results Example 7 above the ED$_{50}$ and selectivity values were obtained for the compounds set out in Table B.

TABLE B

| COMPOUND | ED$_{50}$ μg/ml | SELECTIVITY |
|---|---|---|
| 1-(2-phenylethyl)imidazole | 20 | + |
| 1-(3-phenylpropyl)imidazole | 25 | + |
| 1-(3-phenylprop-2-enyl)imidazole | 17 | (+) |
| 1-(2-phenylpropyl)imidazole | <5 | ++(+) |
| 1-benzylimidazole | 5 | +++ |
| 1-(3-nitrobenzyl)imidazole | 55 | |
| 1-(3-aminobenzyl)imidazole | ~10 | ++ |
| 1-(2,4-dichlorobenzyl)imidazole | 2–8 | ++(+) |
| 1-(4-fluorobenzyl)imidazole | 28 | (+) |
| 1-(4-methylbenzyl)imidazole | 30 | + |
| 1-(2-bromobenzyl)imidazole | 2.4, 0.5 | +++(+) |
| 1-(4-bromobenzyl)imidazole | 4.6 | (+) |
| 1-(3-bromobenzyl)imidazole | 14.5 | +++ |
| 1-(4-i-propylbenzyl)imidazole | 0.1 | 0 |
| 1-[3-(2,4-dichlorophenyl)-propyl]imidazole | 0.6 | ++ |
| 1-(2,3-dimethylphenyl)imidazole | ~3 | ++ |
| 1-(2-chlorobenzyl)imidazole | 0.5 | ++ |

EXAMPLE 33

By the methods described in the Tablet Formulation Examples above tablets were prepared of:

1-(2-phenylethyl)imidazole,
1-(3-phenylpropyl)imidazole,
1-(3-phenylprop-2-enyl)imidazole,
1-(2-phenylpropyl)imidazole,
1-benzylimidazole,
1-(3-nitrobenzyl)imidazole,
1-(3-aminobenzyl)imidazole
1-(2,4-dichlorobenzyl)imidazole,
1-(4-fluorobenzyl)imidazole,
1-(4-methylbenzyl)imidazole,
1-(2-bromobenzyl)imidazole,
1-(4-bromobenzyl)imidazole,
1-(3-bromobenzyl)imidazole,
1-(4-i-propylbenzyl)imidazole,
1-[3-(2,4-dichlorophenyl)propyl]imidazole,
1-(2,3-dimethylphenyl)imidazole,

EXAMPLE 34

Injectable Formulations

Injectable formulations were prepared by the method of Injectable formulation Example 12 above using the imidazoles mentioned in Example 33.

I claim:

1. 1-[3-(2,4-Dichlorophenyl)propyl]imidazole, or a pharmaceutically acceptable acid addition salt thereof.

2. 1-[3-(2,4-Dichlorophenyl)-propyl]imidazole.

* * * * *